United States Patent [19]

Ansley

[11] Patent Number: 5,219,578

[45] Date of Patent: Jun. 15, 1993

[54] COMPOSITION AND METHOD FOR IMMUNOSTIMULATION IN MAMMALS

[75] Inventor: Daniel R. Ansley, Ottawa, Kans.

[73] Assignee: InnoVet, Inc., Boca Raton, Fla.

[21] Appl. No.: 660,401

[22] Filed: Feb. 25, 1991

[51] Int. Cl.⁵ ............... A61K 35/16; A61K 39/395
[52] U.S. Cl. ............................ 424/531; 424/530; 424/85.8
[58] Field of Search ............... 424/85.8, 530, 531; 530/82

[56] References Cited

U.S. PATENT DOCUMENTS

| | | |
|---|---|---|
| 2,770,616 | 11/1956 | Cohn et al. . |
| 3,410,839 | 11/1968 | De Carvalho . |
| 3,429,867 | 2/1969 | Bozicevich . |
| 3,664,994 | 5/1972 | Perper . |
| 3,687,928 | 8/1972 | Brouwer et al. . |
| 3,745,155 | 7/1973 | Dahlgren et al. . |
| 3,763,135 | 10/1973 | Shanbrom et al. . |
| 3,808,189 | 4/1974 | Breuer . |
| 3,917,818 | 11/1975 | Botes . |
| 4,075,193 | 2/1978 | Campbell et al. . |
| 4,082,734 | 4/1978 | Stephan . |
| 4,087,519 | 5/1978 | Trepo . |
| 4,093,606 | 6/1978 | Coval . |
| 4,096,244 | 6/1978 | Newson et al. . |
| 4,124,576 | 11/1978 | Coval . |
| 4,126,605 | 11/1978 | Schneider et al. . |
| 4,136,094 | 1/1979 | Condie . |
| 4,154,819 | 5/1979 | Stephan . |
| 4,164,495 | 8/1979 | Hansen . |
| 4,165,370 | 8/1979 | Coval . |
| 4,256,631 | 3/1981 | Yokoo et al. . |
| 4,318,902 | 3/1982 | Stephan . |
| 4,322,403 | 3/1982 | Bünnig . |
| 4,362,661 | 12/1982 | Ono et al. . |
| 4,371,520 | 2/1983 | Uemura et al. . |
| 4,379,086 | 4/1983 | Kimura et al. . |
| 4,384,993 | 5/1983 | Sato et al. . |
| 4,434,093 | 2/1984 | Zolton et al. . |
| 4,476,109 | 10/1984 | Kimura et al. . |
| 4,482,483 | 11/1984 | Curry et al. . |
| 4,499,073 | 2/1985 | Tenold . |
| 4,572,834 | 2/1986 | Stout . |
| 4,590,002 | 5/1986 | Zolton et al. . |
| 4,597,966 | 7/1986 | Zolton et al. . |
| 4,623,541 | 11/1986 | Elliot et al. . |
| 4,639,523 | 1/1987 | Hou et al. ............... 424/85.8 |
| 4,665,159 | 5/1987 | Dobkin . |
| 4,687,665 | 8/1987 | Stout . |
| 4,692,331 | 9/1987 | Uemura et al. . |
| 4,702,908 | 10/1987 | Thorbecke et al. . |
| 4,717,766 | 1/1988 | Dobkin . |
| 4,719,107 | 1/1988 | Carosella et al. . |
| 4,719,290 | 1/1988 | Curry et al. . |
| 4,762,714 | 8/1988 | Mitra et al. . |
| 4,835,257 | 5/1989 | Friedrich-Fiechtl et al. . |
| 4,845,199 | 7/1989 | Hirao et al. . |
| 4,857,121 | 5/1986 | Collins et al. ............... 424/85.8 |
| 4,868,109 | 9/1989 | Lansdorp . |
| 4,874,708 | 10/1989 | Makula et al. . |
| 4,883,662 | 11/1989 | Stout . |
| 4,885,165 | 12/1989 | Skurkovich . |
| 4,891,219 | 1/1990 | Karr, Jr. et al. . |
| 4,897,265 | 1/1990 | Stolle et al. . |
| 4,911,910 | 3/1990 | Mifflin . |
| 4,937,071 | 6/1990 | Cioco et al. . |
| 4,948,877 | 8/1990 | Mitra et al. . |
| 4,956,349 | 9/1990 | Beck . |
| 4,957,739 | 9/1990 | Berget et al. . |

FOREIGN PATENT DOCUMENTS

| | | | |
|---|---|---|---|
| 0025018 | 2/1977 | Japan ............... | 424/85.8 |
| 0649036 | 2/1979 | U.S.S.R. ............... | 424/85.8 |

Primary Examiner—Douglas W. Robinson
Assistant Examiner—Jean C. Witz
Attorney, Agent, or Firm—D. A. N. Chase; Michael Yakimo, Jr.; Richard P. Stitt

[57] ABSTRACT

A method of stimulating the immune system of mammals is claimed comprising treating a second mammal with a gamma immunoglobulin containing fraction obtained from a first mammal which has not been exposed to foreign antigens.

7 Claims, No Drawings

COMPOSITION AND METHOD FOR IMMUNOSTIMULATION IN MAMMALS

This invention relates to a composition which is utilized to stimulate the immune system of mammals. More particularly, the present invention relates to the isolation of a gamma immunoglobulin (IgG) fraction from goats free from foreign or artificially induced antigens and the utilization of the isolated immunoglobulin G (IgG) fraction to induce a stimulated immune response in mammals.

BACKGROUND OF THE INVENTION

It has long been known that mammals, when confronted with bacterial or viral infections, exhibit efforts at self-healing which are initiated by a complex physiological network referred to as the immune system. The immune system operates in response to a challenge to the mammalian system by initially recognizing the presence of a foreign organism or pathogen within the animals body. This is followed by an attack on the foreign organism by the T-cells, B-cells and other "killer" cells of the mammalian system. This immune response functions or is "turned on" by a variety of immune system regulators which function to selectively activate the various aspects of the immune system depending upon the type of insult confronting the subject animal.

A substantial component of the immune system is a group of structurally related glycoproteins contained within the blood and extra cellular fluids collectively known as immunoglobulins. Five immunoglobulin classes have been identified and are denominated as immunoglobulin G (IgG), IgM, IgA, IgD and IgE. The basic structural unit of each immunoglobulin class consists of two pairs of polypeptide chains joined by disulfide bonds. The five classes of immunoglobulins have different biological properties and different distributions in the body. The structure responsible for the biological properties of each immunoglobulin class is located on that part of the immunoglobulin molecule which is unique for each class—the Fc fragment. While some antibodies are produced at all times in normal animals, specific antibodies—a unique subset of immunoglobulins—may be produced only in response to specific antigenic stimulation.

IgG is the major antibody class in normal mammalian systems and forms about 70% of the total immunoglobulin. IgG is evenly distributed between intra- and extravascular pools. It is the first major antibody of secondary immune responses and the exclusive antitoxin class. IgG is a monomeric protein and can be divided into four sub-chains—two heavy chains and two light chains. Taking the four sub-chains together each IgG molecule consists of one $H_2L_2$ unit with a molecular weight of approximately 140,000 Daltons. Molecules of the IgG class are actively transported across the placenta and provide passive immunity to the newborn infant at a time when the infant's immune mechanisms are not developed.

The remaining four immunoglobulin classes are more narrow components of the immune system.

IgM is the first immunoglobulin class produced by the maturing fetus. IgM does not normally cross the placenta from the mother to fetus, but may be produced actively by the fetus prior to birth, especially if the fetus has been exposed to antigens by infection. IgA is found in relatively small amounts in serum and tissue fluids, but is present in high concentrations in external secretion such as saliva, tears, and bronchial secretions. IgE is also present in very low concentrations and appears to be associated with the histamine response. The last immunoglobulin class IgD is present in very low concentrations in the serum. IgD appears to be related to stimulating immature lymphocytes to multiply and to differentiate and to secrete antibodies of other classes. Therefore, it appears that all immunoglobulin classes are important in the immune systems of mammals.

Modulation of the immune system to effect greater response to foreign agents has been an area of interest for some years. The development of specific antibodies through vaccination has long been utilized to provide mammals with long term immune defense mechanisms to specific micro organisms forms.

Recent efforts in immunology have been directed towards the utilization of the immune system regulating molecules themselves to provide increased immune system activity. It is believed that through the use of immune regulating or immune modulating molecules that a state of general hyperactivity of the immune system is induced which may be useful in combating an infection in a mammal challenged by a micro organism. It is believed that such as induced state of general immune hyperactivity would result in a therapeutic response to the challenge. This might be viewed as just the opposite of the vaccination type response which produces a specific long term immunity. If such a non-specific immune response could be initiated at will it could be utilized to either act alone or in conjunction with a conventional treatment directed towards the etiological agents. Such a mechanism could be based upon activation of phagocytic cells which are capable of responding to a wide range of infectious agents. It may also be that the T-lymphocytes, which are major mediators of the overall immune response, may act to enhance the operation of non-specific cellular immunity even though the T-lymphocytes themselves are a part of the specific immune response.

Therefore, it is an object of the present invention to provide a means for modulating the immune response in mammals afflicted with disease.

Another object of the present invention is to provide a means for enhancing the ability of conventional antimicrobial medicaments by providing a concomitant stimulation and potentiation in the mammalian immune response.

Yet another object of the present invention is to provide a means of stimulating the immune response in mammals to heighten the mammals ability at self-heating when challenged by an infectious agent.

The above and further objects and novel features of the invention will more fully appear from the following description and the examples contained therein.

SUMMARY OF THE INVENTION

The invention method and inventive compounds derived thereby involve, generally, the isolation of an IgG containing fraction from the blood of a first mammal such as a goat. This first mammal has not been pre-treated in any way nor have foreign antigens been introduced to the mammal. The IgG containing fraction obtained from this first mammal is then used to treat a second mammal. The second mammal can be of the same or of a different species as the first. In treating the second mammal with the IgG containing fraction from the first mammal, the immune system of the second mammal becomes stimulated and the second mammal is thereby assisted in overcoming the deleterious effects of a disease or malady.

The present invention is broadly concerned with a unique method for cross species stimulation of the immune system. More particularly the present invention involves isolation of an IgG containing fraction from a goat which is free from artificially induced foreign antigens. The IgG containing fraction is then used for treating a mammal to produce improved ability of the mammal to respond to immune system challenges. It is believed that treating a mammal with the composition of the present invention stimulates the immune system response in the subject mammal by inducing activation of interferon, macrophages, T-lymphocytes and natural killer cells. Thus the subject animal is able to ward off the deleterious effects of a challenge by the infectious micro-organism.

Broadly stated the method of the present invention comprises obtaining an amount of blood from a goat which is at least 6 months of age and which is either a non-bred female or castrated male and which has not been subjected to immune stimulation from artificially induced foreign antigens. The specification of the goat being at least six months old, and either a non-bred female or a castrated male are preferences for increasing the isolated product and not stated by way of limitation. The blood is then processed to obtain an IgG containing fraction. The animal to be treated then receives an injection of the fraction containing the caprine IgG in an appropriate vehicle. In addition to being treated with the present invention animals may concurrently receive conventional regimens of therapy for the particular disease.

DESCRIPTION OF THE PREFERRED EMBODIMENT

The following examples present the preferred method of producing the inventive compound in conjunction with a number of examples demonstrating the treatment of mammals with the present invention.

EXAMPLE 1

The following example presents the preferred procedures for the production of the biological compound of the present invention with the mammalian blood being obtained from a goat.

Blood Collection

A quantity of blood is obtained from goats (approximately 500 ml from each goat) which are preferably at least six months of age and have not been preconditioned or vaccinated with any foreign antigens which might create an antibody response in the goat. It is preferred that these non-immune stimulated goats be either non-bred females or castrated males. Pregnant females are to be avoided as IgG will migrate across the placenta and this will result in reduced isolation of the final product. In the present example Nubian goats were utilized as the large species size reduces the number of subjects required to present a consistent supply of blood for isolation purposes. All animals should be in a state of good health.

The blood is collected by first restraining the goat to prevent unnecessary movement and to also prevent injury during the collection procedure. The neck is then clipped and treated with an antiseptic solution. A sterile bleeding needle is inserted into the jugular vein allowing blood to pass through sterile tubing and into a sterile one liter wide mouth bottle.

The blood is then refrigerated for four hours to allow clotting to occur. After the clot has developed the serum is separated from the clot by aspiration or, alternatively, it may be decanted. The serum is then divided among 50 ml centrifuge tubes. The serum is centrifuged at approximately 3,000 rpm for approximately 20 minutes to remove any remaining red blood cells and materials of similar density. After centrifugation the serum is then decanted from the solid portion or pellet, pooled and the total serum volume noted.

Serum Sodium Sulfate Fractionation

The pooled serum from the previous procedure is permitted to warm to approximately 25° centigrade or room temperature. Approximately 250 ml of the serum is placed in a one liter glass beaker with constant mild stirring. To the stirring serum is slowly added 90 grams of solid anhydrous sodium sulfate. The sodium sulfate is added in small quantities and allowed to dissolve before additional sodium sulfate is added to the serum. When the addition of the sodium sulfate is complete the mixture is allowed to continue stirring for approximately one hour.

The serum-sodium sulfate mixture is then divided into 50 ml centrifuge tubes and centrifuged at approximately 3,000 rpm for approximately 30 minutes. The clear supernatant is then gently decanted from the pellet. The supernatant solution may be discarded.

The pellet is then resuspended in solution through the addition of deionized water and gentle stirring with a glass rod. Once the pellet has been redissolved the total volume of the solution should be adjusted to the original serum volume as measured after the first centrifugation step.

Dialysis Procedure

To remove excess sulfate ions, the resuspended pellet or salt cut volume is dialyzed against phosphate buffered saline (PBS) at 4° centigrade with constant stirring. The phosphate buffered saline is made by adding 8.52 grams of sodium phosphate and 52.58 grams of sodium chloride to 6 liters of deionized water and the solution adjusted to a pH of approximately 7.4.

Dialysis tubing having a molecular weight cutoff of 30,000 daltons is cut into lengths of 18 inches and placed into a beaker of boiling distilled water. The dialysis tubing is then removed from the boiling water and rinsed with cool distilled water. After tying off one end of the dialysis tubing, the tubing is filled with the redissolved salt cut fraction, the open end tied off, and the tubing placed into the phosphate buffered saline. The phosphate buffered saline volume should be approximately 12 times greater than the volume of the resuspended pellet volume. The PBS solution should be changed four times at approximately 6 to 8 hour intervals.

Upon completion of the dialysis of the resuspended salt cut IgG fraction the dialysis tubes are opened and the substantially sulfate ion-free product is divided into 50 ml centrifuge tubes and centrifuged at approximately 3,000 rpm for approximately 30 minutes. The supernatant from this centrifugation is then filtered through a 0.2 micron filter to produce a sterile final product.

Protein Concentration

The final product is then tested to determine the protein concentration per milliliter of solution. This is accomplished by ultraviolet measurement of the solution at 280 nm. The protein concentration is then determined by comparison with a table of known protein standards. Alternatively the protein concentration may be determined utilizing the Biuret-Lowery method.

Sample Contamination

The final product is examined for the presence of unwanted bacteria and fungal contamination. A sample of the final product is plated onto appropriate agars by stabbing and streaking. The agar plates are then incubated at 37° for 72 hours and read for the presence of contamination at 24 hours and 72 hours.

Determination of IgG Concentration

The IgG concentration of the final product is determined using a commercially available radial immuno diffusion kit. In this procedure the final product is placed in a central well of an agarose gel which has been impregnated with horse anti-goat IgG antiserum. As the final IgG product diffuses from the well into the agarose gel it becomes less concentrated. At some distance from the central well the final product and the horse anti-goat IgG antiserum are in optimal proportions for precipitation to occur. At the point of precipitation a ringed shaped precipitate forms. The area inside the ring is directly proportionate to the concentration of the final product. The horse anti-goat IgG antiserum standard is available from Sigma Chemical Company of St. Louis, Mo.

Molecular Weight Determination

Molecular weight of the final IgG fraction is determined by SDS-polyacrylamide gel electrophoresis. The analysis conditions consist of a 4% stacking gel, 10% running gel (0.75 mm thick), 200 volts (constant) for 40 minutes with 0.05% bromphenol blue as tracking dye. The running buffer is Tris-Glycine, at pH 8.3. The gels are fixed and stained in 40% methanol-10% acidic acid containing 0.1% coomassie brilliant blue R-250. The gels are decolorized with methanol-acidic acid and stored in deionized water.

A 54 microgram sample of the inventive compound was run on the gel against a mixture of standard polypeptides of known molecular weights.

The SDS-gel electrophoresis results indicate that the inventive compound consists principally of an IgG fraction (which in the gel electrophoresis divided into the characteristic heavy chain/light chain of the IgG molecule) and an additional component having a molecular weight of approximately 65,000 which is believed to be a serum albumin component.

EXAMPLE 2

Treatment of Equine Lower Respiratory Disease

It is common that horses are frequently transported from race track to race track or to an equine training center thereby coming in contact with numerous other horses which have been similarly transported. This proximity to horses that have been under the stress of transportation and which have been in contact with different populations of horses promotes the spread of equine lower respiratory disease (ELRD) caused by a variety of opportunistic organisms. Treatment of horses exhibiting ELRD is a frequent activity for veterinarians. It is the standard treatment for horses exhibiting ELRD to receive 3 grams of Oxytetracycline in 50 ml of Dimethyl Sulfoxide and diluted with Ringers Solution to a volume of 250 mls. This solution is given to the horse by intravenous injection repeated daily for 7 days.

To evaluate the efficacy of the present invention as a supplement to this standard therapy for ELRD a test population of horses exhibiting symptoms of lower respiratory disease was selected. The horses initially presented as exhibiting the standard clinical signs of ELRD. All subjects were submitted to bronchoscopic examination to determine the extent of illness.

The animals admitted for the study exhibited evidence of lower respiratory disease based upon three factors: (1) suppurative bronchial discharge detected by bronchoscopy; (2) one or more clinical signs of respiratory disease (i.e. cough, nasal discharge, abnormal chest sounds); and (3) poor exercise performance and necessity of limiting or terminating training of the animal. However, animals which exhibited upper (mechanical) airway disease or other disease which could impair the resolution of the lower airway infection or which would entail therapy in addition to the treatment of ELRD were excluded as subjects for the present study.

As the study was regarded only as a feasibility study, horses were randomly selected for supplemental treatment with the invention and all animals were treated with the standard Oxytetracycline/DMSO standard antibiotic regimen daily for 7 days. As the study progressed, animals not dosed with the invention and not responding to the standard antibiotic therapeutic regimen were subsequently given a second treatment consisting of the standard antibiotic treatment plus dosing with the present invention. The dosage of the invention was 60 mg in 3 ml of solution.

A total of nine horses were included in the feasibility study. Six of the animals, numbers 1, 2, 4, 5, 7, and 8, (see Chart 1) were initially dosed with the invention as well as the standard antibiotic treatment. Three animals, numbers 3, 6, and 9, were not initially treated with the inventive therapy and received only the standard antibiotic treatment. These three cases were considered as controls.

Of the six animals initially receiving the inventive therapy, four of the six, numbers 1, 2, 7, and 8, were determined to be cured of the lower respiratory infection upon the conclusion of the first regimen of treatment. Two of the six animals receiving the inventive therapy, numbers 4 and 5, received a second regimen of the standard treatment and the inventive treatment. In the case of subject number 5 the animal was a severe case which was nearly healed after the first treatment regimen, however, a second treatment regimen was given the animal to insure success. In the case of horse number 4, the animal presented a very severe case of lower respiratory disease and it was determined that a second 7 day regimen of both the standard treatment and the inventive treatment was in order. At the conclusion of the second 7 day period the animal was determined to be healed.

Chart 1

| Subject | Invention Treatment | Standard Treatment | Days Post Treatment | Nasal[1] Discharge | Auscultation[2] | Cough[3] Freq. | Bronchoscopy[4] Type | Dist. | Amt. |
|---|---|---|---|---|---|---|---|---|---|
| 1 | yes | yes | 0 | Purulent | Moist Rales | 3–6 | Purulent | 30–60% | >50% |
|   | — | — | 12 | none | normal | none | Mucoid | <30% | >50% |
| 2 | yes | yes | 0 | Mod. Puru. | Mucoid Cong. | 3–6 | Purulent | 30–60% | >50% |
|   | — | — | 8 | none | normal | none | normal | none | none |
| 3 | no | yes | 0 | Mod. Puru. | Congest. | 3–6 | Purulent | Diffuse | >50% |
|   | yes | yes | 7 | Purulent | normal | none | Purulent | <30% | >50% |
|   | — | — | 12 | none | normal | none | normal | none | none |
| 4 | yes | yes | 0 | Purulent | Moist Rales | 3–6 | Purulent | 60–90% | >50% |
|   | yes | yes | 7 | none | normal | none | Purulent | >30% | >50% |
|   | — | — | 7 | none | normal | none | normal | none | none |
| 5 | yes | yes | 0 | Purulent | Moist Rales | 0–3 | Purulent | 60–90% | >50% |
|   | yes | — | 7 | none | normal | 0 | Mucoid | <30% | <50% |
| 6 | no | yes | 0 | Purulent | Moist Rales | 3–6 | Purulent | 60–90% | >50% |
|   | yes | yes | 7 | Purulent | Moist Rales | 3–6 | Purulent | 30–60% | >50% |
|   | — | — | 7 | none | normal | none | normal | none | none |
| 7 | yes | yes | 0 | Purulent | normal | 0 | Purulent | 60–90% | <50% |
|   | — | — | 7 | none | normal | none | normal | none | none |
| 8 | yes | yes | 0 | Purulent | Moist Rales | 3–6 | Purulent | 60–90% | >50% |
|   | — | — | 7 | none | normal | none | Purulent | none | none |
| 9 | no | yes | 0 | Purulent | Moist Rales | >6 | Purulent | 60–90% | >50% |
|   | yes | yes | 7 | none | normal | 3–6 | Purulent | 30–60% | >50% |
|   | — | — | 7 | none | normal | none | none | none | none |

*Dosage conducted after determination of the first seven day test results listed.
[1]Nasal Discharge = none, slight serous, moderate seromucous, marked mucoid, purulent.
[2]Chest Auscultation = normal; Moist Rales; Mucoid Congestion; Congestion.
[3]Cough Frequency = episodes per minute.
[4]Bronchoscopy
Type = none, serous, mucoid, purulent
Dist. (distribution over tracheal mucosa) - less than 30%, 30–60%, 60–90%, diffuse.
Amt. (amount of discharge) - normal; less than 50% more than normal; copius over 50% more than normal.

Animals number 3, 6, and 9, initially deemed to be controls, exhibited little treatment success in the first 7 day treatment regimen. It was, therefore, concluded that the second regimen period would include dosing with the inventive treatment in addition to dosing with the standard Oxytetracycline/DMSO treatment. In all three cases the second regimen, including use of the inventive treatment for animals numbered 3, 6, and 9, provided satisfactory results within 7 days.

It should be appreciated that while 60 mg of the inventive composition were used in the present example, it may be necessary to adjust this amount to be effective in the particular mammalian subject and particular malady. It is to be understood that as each subject upon which the treatment is utilized is, to a degree a unique individual, a certain degree of variation in responsiveness to the treatment will be presented. In addition, variation and response will be noticed depending upon the disease with which the subject is afflicted and the seriousness of the disease state in a particular subject. Therefore, while certain amounts of the inventive compound are stated herein it will be appreciated that a variance in the amount required to be effective will be observed depending upon the previously stated subject and disease parameters which will impact upon the amount of the compound which is efficicaous in any particular subject and disease. In light of these variables it will be understood that some degree of modification of the amount of the inventive compound utilized with any particular subject, species or disease will be necessary to overcome a deleterious effect of a malady in any particular subject.

EXAMPLE 3

Treatment Of Ovine Footrot

Ovine footrot is a contagious and debilitating disease of sheep and lambs caused by various serotypes of Bacteroides nodosus. The disease is characterized by lameness and separation of the hoof corneum from the basal epithelium and derma. The disease exists in high incidence in all sheep producing countries of the world. Ovine footrot rivals respiratory disease as being one of the most economically significant sheep health problems in the United States. Therefore, it was sought to determine whether a non-adjuvanted immunostimulant would enhance the ability of sheep to immunologically recognized the pili antigens of B. nodoses and stimulate a therapeutic immune response in infected sheep.

A preliminary examination of this question was conducted by investigating the response of eight sheep naturally infected with B. nodoses. Three non-infected sheep were housed with the infected sheep under conditions favorable to the transfer of the B. nodoses infection. Half of the infected animals were given two treatments of the inventive compound. The first treatment consisted of 1 ml (20 mg/ml) administered subcutaneously behind the ear. The second treatment was administered 10 days later. The untreated animals served as controls. No additional therapy such as foot baths were allowed during the experimental period. All animals were commingled in a single paddock for the duration of the study.

At the conclusion of the 10 day trial blood specimens were drawn on all subjects and white cell profiles were determined.

As is shown in Chart 2, there was a substantial increase in circulating monocytes of the animals treated with the inventive compound. It should be noted that there was an absence of an increase in the percentage of monocytes in the control animals. The percentage of monocytes in the blood was selected as a positive response indicative of immunostimulation by the inventive compound. As the circulating monocyte is the counter part of the fixed tissue macrophage and is capable of phagocytosis, it therefore is believed that an increase in this blood component is a reliable indicator of stimulation of the subjects immune system.

EXAMPLE 4

Gross Evaluation Of Treatment Of Ovine Footrot

A second study was conducted utilizing the inventive treatment for ovine footrot with the subjects being two geographically separated flocks of sheep. One group was a commercial sheep flock in central California and the second was a farm flock located in eastern Kansas. The first flock consisted of 200 ewes all of which exhibited symptoms of ovine footrot. All four feet were inspected for signs of footrot, then graded and trimmed. Grading of the feet and hooves was on the following scale:
0 = No Disease Or Hoof Damage
1 = some scalding inter-digitally
2 = some under turning of the hoof
3 = separation of hoof from corneum
4 = no hoof Chart 2
SUMMARY OF OVINE WHITE CELL PROFILES

| SHEEP | CONTROL | TREATED | LYMPHS (50–70%) | MONOS (1–8%) |
|---|---|---|---|---|
| U-1 | XXX |  | 68.5 | 16.0 |
| U-2 |  | XXX | 40.0 | 54.2 |
| U-3 | XXX |  | 71.8 | 18.1 |
| U-4 |  | XXX | 48.1 | 43.6 |
| L-1 |  | XXX | 65.9 | 26.6 |
| L-2 | XXX |  | 83.0 | 09.7 |
| L-3 | XXX |  | 73.4 | 12.5 |
| L-4 |  | XXX | 56.3 | 34.8 |
| L-5 |  | XXX | 61.6 | 32.3 |

Each of the subject animals received an injection of 1 ml of the inventive compound (20 mg/ml) intramuscularly administered on the right side of the neck. After 10 days the animals received a second injection of 1 ml of the inventive compound (20 mg/ml) injected intramuscularly on the left side of the neck.

The second experimental flock consisted of 150 ewes and lambs in which evidence of footrot was rampant. The feet of each animal were then checked and graded. Each of the animals had at least one foot which was of grade four disease state. All animals in this group were treated with 1 ml (20 mg/ml) of the inventive compound which was injected on the right side of the neck. After 10 days all animals received a second injection of 1 ml (20 mg/ml) on the left side of the neck.

Within 5 days of the initial injection obvious improvement of the California infected flock was noted. All treated animals had responded in terms of increased mobility, and brighter eyes. Within 15 days physical improvement was significant in terms of hoof regeneration. The eastern Kansas flock responded in exactly the same manner as did the California flock. Clinical signs of footrot in the Kansas flock were completely eliminated in both ewes and lambs. An examination of the injection sites for animals revealed that they were free of swelling, abscesses and granulomas.

The consistent curative result for both flocks was found to be free of any observable harmful side effects. The use of the inventive treatment in pregnant ewes did not induce abortion or result in stillbirth. One positive side effect was noted in the eastern Kansas flock which was a significant increase in weight gain in treated lambs.

EXAMPLE 5

Bovine Shipping Fever

The transportation of cattle to feedlots or to other staging areas where a large number of cattle are commingled can bring about symptoms generally categorized as shipping fever. Shipping fever comprises a number of symptoms which result from the stress calves have undergone while being transported. The presence of shipping fever can leave a calf susceptible to a variety of other disease due to the reduced immune state of the calf. Traditionally calves have been treated for this malady by a standard treatment comprising an antibiotic and vitamin regimen.

To determine the efficacy of the present invention with respect to shipping fever it was determined to randomly allocate animals into one of two treatment groups upon their arrival at a feedlot facility. Both groups received the standard treatment consisting of immunization with viral vaccines and Clostridial and Haemophilous bacterins. The animals also received the same antibiotic and vitamin treatment regimen while being treated.

One group of 10 animals, in addition to the standard treatment, received a 2 ml (20 mg/ml) of the inventive compound by intramuscular injection. The other group of 10 animals received 2 mls of sterile saline by intramuscular injection.

At the conclusion of the 10 day observation period (see Chart 3) the group of animals receiving the inventive compound presented an average weight gain of 61 lbs. The animals which did not receive the inventive compound showed an average weight gain of 50 lbs.

EXAMPLE 6

Treatment For Bovine Respiratory Disease

In the transport of newly weaned cattle, weighing approximately 500–600 pounds, it is not uncommon for the animals to develop respiratory disease during the course of being shipped to a feedlot or other staging area. It is customary for such animals upon arrival at a feed lot to receive a standard treatment consisting of immunization with modified live viral vaccines and Clostridial and Haemophilous bacterins. The object is to assist the animals to recover from the respiratory disease and to provide specific immunity to these diseases.

| Calf No. | Chart 3 | | |
|---|---|---|---|
| | Initial Day 0 Weight (lb.) | Final Day 10 Weight (lb.) | Δlb. |
| Calves Treated With Inventive Compound: Treated (T) | | | |
| 99 | 566 | 601 | 35 |
| 100 | 530 | 609 | 79 |
| 101 | 565 | 628 | 63 |
| 102 | 691 | 765 | 74 |
| 104 | 615 | 683 | 68 |
| 105 | 483 | 551 | 68 |
| 106 | 403 | 466 | 63 |
| 107 | 593 | 642 | 49 |
| 108 | 446 | 498 | 52 |
| 109 | 466 | 525 | 60 |
| | Avg. Wt. = 536# | Avg. Wt. = 597# | Avg. Wt. Gain = 61 |
| Calves treated With Sterile Saline: Controls (C) | | | |
| 111 | 505 | 565 | 60 |
| 112 | 537 | 573 | 36 |
| 116 | 671 | 742 | 71 |
| 120 | 440 | 494 | 54 |

-continued

Chart 3

| Calf No. | Initial Day 0 Weight (lb.) | Final Day 10 Weight (lb.) | Δlb. |
|---|---|---|---|
| 123 | 526 | 568 | 42 |
| 124 | 558 | 629 | 71 |
| 125 | 500 | 502 | 02 |
| 126 | 598 | 655 | 57 |
| 127 | 531 | 586 | 55 |
| 128 | 462 | 514 | 52 |
| | Avg. Wt. = 533# | Avg. Wt. = 597# | Avg. Wt. Gain = 50 |

Animals were randomly allocated into one of two treatment groups upon the initiation of treatment for respiratory disease. All animals received the same antibiotic, vitamin B, vitamin C treatment regimen. The animals in one group received the inventive compound at the same time as receiving the initial treatment for respiratory disease. The second group received an injection of sterile saline solution at the time of the initial treatment and acted as a control. At the conclusion of the treatment period a final weight measurement was taken.

As may be seen in Chart 4 the 10 calves sick with respiratory disease and treated with the inventive compound lost significantly less weight. The calves treated with the inventive compound lost a total of 9 lbs. of body weight while the calves receiving the sterile saline lost a totally 60 lbs. of body weight over the treatment period. The calves suffering from respiratory disease and treated with the inventive compound average 15 lbs. of body weight gain per calf while the calves receiving only sterile saline averaged only 13 lbs. of body weight gain per calf.

Chart 4
Respiratory Disease

| Calf No. | Initial Weight (lb) | Final Weight | Weight Loss |
|---|---|---|---|
| Calves Treated With Inventive Compound | | | |
| 1 | 8 | 511 | 526 | — |
| 2 | 20 | 678 | 676 | 2 |
| 3 | 34 | 492 | 519 | — |
| 4 | 74 | 541 | 562 | — |
| 5 | 108 | 446 | 458 | — |
| 6 | 40 | 539 | 534 | 5 |
| 7 | 188 | 524 | 522 | 2 |
| 8 | 192 | 456 | 469 | — |
| 9 | 196 | 467 | 486 | — |
| 10 | 200 | 633 | 691 | — |
| | Avg. Wt. = 529 | Avg. Wt. = 544 | Total Loss = 9 lbs |
| Calves Treated With Sterile Saline | | | |
| 1 | 39 | 550 | 564 | — |
| 2 | 19 | 582 | 592 | — |
| 3 | 27 | 546 | 511 | 35 |
| 4 | 55 | 563 | 549 | 14 |
| 5 | 75 | 694 | 691 | 3 |
| 6 | 94 | 564 | 613 | — |
| 7 | 145 | 382 | 374 | 8 |
| 8 | 173 | 472 | 476 | — |
| 9 | 177 | 531 | 571 | — |
| 10 | 87 | 713 | 788 | — |
| | Avg. Wt. = 560 | Avg. Wt. = 573 | Total Loss = 60 lbs |

EXAMPLE 7

Treatment of Canine Parvovirus Infections

To test the efficacy of the inventive compound in the treatment of canine parvovirus an examination was conducted on 75 dogs and puppies. Each animal was observed as exhibiting symptoms of affliction with parvovirus. Subsequently, each animal was dosed with 1 ml of the inventive compound at a concentration of 20 milligrams per milliliter. The administration was by subcutaneous injection. The animals were treated for the disease while still in an alert and responsive state. A recovery rate of between 90 and 95 percent obtained.

EXAMPLE 8

Treatment of Canine Lymphoma

A preliminary study of the inventive compound in the treatment of canine lymphoma was conducted. Two adult animals presenting lymphomas were given two 1 ml treatments 10 days apart. The inventive compound was administered subcutaneously, the concentration being 20 milligrams per milliliter. The preliminary results of this treatment indicate a complete remission of the lymphoma in both animals with no recurrence in the 12 month period subsequent to treatment.

EXAMPLE 9

Treatment of Bovine Lymphoma

A single animal presenting with an advanced lymphoma was treated with the inventive compound. The animal exhibited some paralysis in the hind quarters and was in the third trimester of pregnancy. A single treatment of 4 mls was administered intravenously having a concentration of 20 milligrams per milliliter. Improvement in the animal was noted within 24 hours. The lymphoma node size reduced from a 4 inch diameter to a 1 inch diameter. Subsequently the cow calved without complication and 6 months passed before any reoccurrence of the lymphoma.

As previously stated the dosage and administration of the inventive compound will vary depending upon the mammal treated and the particular disease. In general, treatment may be given by the subcutaneous, intramuscular, or intravenous routes. Usually, only a single is necessary, but treatment may be repeated at 7 to 10 day intervals if necessary. The following is intended to provide a guideline in the calculation of the dosage of the inventive compound:

| Dosage And Administration | | |
|---|---|---|
| Canine | 1 ml | (20 mg) per treatment |
| Feline | 1 ml | (20 mg) per treatment |
| Bovine | 2 ml | (40 mg) up to 500 lbs. per treatment |
| Bovine | 4 ml | (80 mg) 500–1,000 lbs. per treatment |
| Equine | 2 ml | (40 mg) up to 500 lbs. per treatment |
| Equine | 4 ml | (80 mg) 500–1,000 lbs. per treatment |
| Ovine | 1 ml | (20 mg) per treatment |
| Swine | ½ ml | (10 mg) per treatment (piglet) |

It is to be understood that while a certain form of the invention has been described, it is not limited thereto, except insofar as such limitations are included in the following claims and the allowable functional equivalents thereof.

Having thus described the invention, what is claimed as new and desired to be secured by Letters Patent is:

1. A method of stimulating weight gain in cattle comprising the step of injecting said cattle with an effective amount of the immunoglobulin fraction obtained from the serum of a goat free from artificially induced foreign antigens.

2. A method of treating canine parvovirus in a non-caprian mammal by stimulating the immune system comprising the step of: injecting the non-caprian mammal with an effective amount of the immunoglobulin fraction obtained from the serum of a goat free from artificially induced foreign antigens.

3. A method of treating canine lymphoma in a non-caprian mammal by stimulating the immune system comprising the step of: injecting the non-caprian mammal with an effective amount of the immunoglobulin fraction obtained from the serum of a goat free from artificially induced foreign antigens.

4. A method of treating bovine lymphoma in a non-caprian mammal by stimulating the immune system comprising the step of: injecting the non-caprian mammal with an effective amount of the immunoglobulin fraction obtained from the serum of a goat free from artificially induced foreign antigens.

5. A method of treating aquine respiratory disease in a non-caprian mammal by stimulating the immune system comprising the step of: injecting the non-caprian mammal with an effective amount of the immunoglobulin fraction obtained from the serum of a goat free from artificially induced foreign antigens.

6. A method of treating bovine respiratory disease in a non-caprian mammal by stimulating the immune system comprising the step of: injecting the non-caprian mammal with an effective amount of the immunoglobulin fraction obtained from the serum of a goat free from artificially induced foreign antigens.

7. A method of treating ovine foot rot in a non-caprian mammal by stimulating the immune system comprising the step of: injecting the non-caprian mammal with an effective amount of the immunoglobulin fraction obtained from the serum of a goat free from artificially induced foreign antigens.

* * * * *

UNITED STATES PATENT AND TRADEMARK OFFICE
CERTIFICATE OF CORRECTION

PATENT NO. : 5,219,578
DATED : June 15, 1993
INVENTOR(S) : Daniel R. Ansley

It is certified that error appears in the above—identified patent and that said Letters Patent is hereby corrected as shown below:

Claim 5, column 14, line 3, after "treating" delete "aquine" and insert --equine--.

Signed and Sealed this

Second Day of January, 1996

Attest:

BRUCE LEHMAN

Attesting Officer      Commissioner of Patents and Trademarks